United States Patent [19]

Oude Alink

[11] Patent Number: 5,252,289
[45] Date of Patent: Oct. 12, 1993

[54] WATER SOLUBLE 1,2-DITHIO-3-THIONES

[75] Inventor: Bernardus A. Oude Alink, St. Louis, Mo.

[73] Assignee: Petrolite Corporation, St. Louis, Mo.

[21] Appl. No.: 2,532

[22] Filed: Jan. 11, 1993

Related U.S. Application Data

[60] Continuation of Ser. No. 678,850, Apr. 3, 1991, abandoned, which is a division of Ser. No. 558,020, Jul. 26, 1990, abandoned, which is a division of Ser. No. 399,728, Aug. 28, 1989, Pat. No. 4,973,710.

[51] Int. Cl.$^5$ .............................................. C23F 11/12
[52] U.S. Cl. ................................. 422/14; 252/8.555; 252/388; 252/393; 252/395; 252/396; 252/397; 252/404; 252/406; 252/407; 549/37
[58] Field of Search .............. 422/7, 14; 549/37; 252/8.555, 388, 393, 395, 396, 397, 404, 406, 407

[56] References Cited

U.S. PATENT DOCUMENTS

| | | | |
|---|---|---|---|
| 2,647,129 | 7/1953 | Bashour | 260/327 |
| 2,688,620 | 9/1954 | Gaudin | 260/327 |
| 2,729,649 | 1/1956 | Böttcher et al. | 260/327 |
| 3,110,718 | 11/1963 | Thuillier | 260/327 |
| 3,394,146 | 7/1968 | Hodgson et al. | 260/327 |
| 3,697,221 | 10/1972 | Redmore et al. | 21/2.5 |
| 3,791,789 | 2/1974 | Oude Alink | 21/2.5 |
| 3,847,943 | 11/1974 | Warner | 260/327 C |
| 3,994,923 | 11/1976 | Dingwall et al. | 260/327 C |
| 4,382,816 | 5/1983 | Bahr | 71/90 |
| 4,760,078 | 7/1988 | Yamamoto et al. | 514/441 |

FOREIGN PATENT DOCUMENTS 808064 1/1959 United Kingdom.

OTHER PUBLICATIONS

Chem. Abstracts, vol. 73, No. 15, Oct. 12, 1970, p. 359, abstract No. 77104b, Columbus, Ohio; Voronkov et al.: "Reaction of sulfur with organic compounds. XIX. Reaction of sulfur with ethers and esters of p-isopropylphenol".

The Chemistry of Heterocyclic Compounds, "Multi-Sulfur and Sulfur and Oxygen Five-and Six-Membered Heterocycles", Part 1, pp. 347-405, Breslow (ed.), Interscience Publishers, 1969.

*Primary Examiner*—Robert J. Warden
*Assistant Examiner*—Timothy M. McMahon
*Attorney, Agent, or Firm*—Jeffrey S. Boone; Kenneth Solomon

[57] ABSTRACT

Water-soluble 1,2-dithiole-3-thione derivatives are prepared by reacting a polyoxyalkylated starting material with sulfur. These derivatives are useful as corrosion inhibitors, particularly in aqueous environments.

1 Claim, No Drawings

WATER SOLUBLE 1,2-DITHIO-3-THIONES

This is a continuation application of co-pending application U.S. Ser. No. 07/678,850, filed Apr. 3, 1991 now abandoned which application is a division of U.S. patent application Ser. No. 07/558,020, filed Jul. 26, 1990 now abandoned, which application was a division of U.S. patent application Ser. No. 07/399,728, filed Aug. 28, 1989 (now U.S. Pat. No. 4,973,710, granted Nov. 27, 1990).

BACKGROUND OF THE INVENTION

This invention relates to the production of 1,2-dithiole-3-thione derivatives and their use as corrosion inhibitors.

1,2-dithiole-3-thione derivatives are well known, as is their use as corrosion inhibitors. The Chemistry of Heterocyclic Compounds, "Multi-Sulfur and Sulfur and oxygen Five- and Six-Membered Heterocycles", Part 1, Pages 237-386, by David S. Breslow (Chapter Editor), Interscience Publishers, 1969, discusses the synthesis of 1,2-dithiole-3-thiones in detail. U.S. Pat. No. 3,697,221 (Redmore et al Petrolite, 1972) teaches a wide variety of 1,2-dithiole-3thione derivatives and their use as corrosion inhibitors. Despite the utility of the Redmore compounds, their usefulness is limited, possibly due to their lack of water solubility. Further, despite the improved yields reported by Redmore, the reaction to prepare these compounds is not very efficient.

SUMMARY OF THE INVENTION

Briefly, in one respect, the invention provides a water-soluble, polyoxyalkylated 1,2-dithiole-3-thione compound. In another respect, the invention provides a method of making such compounds by reacting specific polyoxyalkylated starting materials with sulfur. In yet another respect, the invention provides a method of inhibiting corrosion in aqueous systems by adding the compounds of the invention to the aqueous system.

The method of the invention is unexpectedly efficient and easy to carry out. The products of the invention are unexpectedly good corrosion inhibitors.

DETAILED DESCRIPTION OF THE INVENTION

In this specification and claims, numeric values are not critical unless otherwise stated. That is, the numeric values may be read as if they were prefaced with the word "about" or "substantially"

A first component useful in the preparation of the compounds of the invention is a polyoxyalkylated compound of the formula:

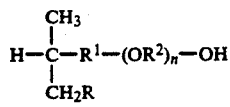

wherein R is H or a $C_1$ to $C_{12}$ organic moiety, desirably H or a $C_1$ to $C_{12}$ alkyl moiety, preferably H or $C_1$ to $C_6$ alkyl moiety, more preferably H; $R^1$ is a $C_1$ to $C_{32}$ organic moiety, desirably a $C_6$ to $C_{12}$ arylene moiety, preferably a $C_6$ aryl moiety; $R^2$ is a $C_1$ to $C_4$ alkylene moiety, preferably a $C_2$ or $C_3$ alkylene moiety, more preferably a $C_2$ alkylene moiety; and n is 1 to 50, desirably 2 to 40, preferably 2.5 to 30, more preferably 3 to 20. A particularly preferred polyoxyalkylated starting compound has the formula:

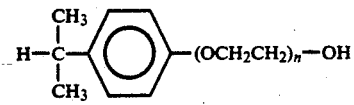

wherein n has an averages about 6.2.

The oxyalkylated starting materials are conveniently prepared by conventional oxyalkylation of the corresponding hydroxyl-containing precursor. Thus, for instance, the preferred precursor material would have the structure:

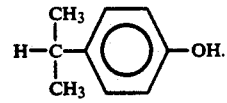

The oxyalkylation reaction is well known to those skilled in the art and can be carried out, for instance, by dissolving the precursor in a solvent, adding a catalytic amount of an alkali metal hydroxide, heating, and adding the desired alkylene oxide.

The compounds of the invention are conveniently prepared by reaction of the oxyalkylated starting material with 6 sulfur atoms, producing 3 H S molecules as a by-product. The reaction preferably takes place with heat (e.g., 210° C.) and a basic catalyst such as di-o-tolyl guanidine. Surprisingly, the sulfurization reaction of the invention takes place with improved yield, compared to the analogous reaction using non-oxyalkylated starting compounds. Thus, although it would be theoretically possible to conduct the oxyalkylation after the sulfurization reaction, the reaction would be considerably less efficient.

The compounds of the invention have the following structure

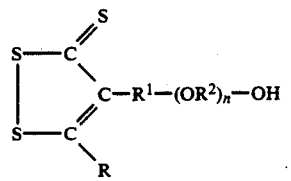

wherein R is H or a $C_1$ to $C_{12}$ organic moiety; $R^1$ is a $C_1$ to $C_{32}$ organic moiety; $R^2$ is a $C_1$ to $C_4$ alkylene moiety; and n is 1 to 50.

The compounds of the invention are water soluble. By "water soluble" is meant having more solubility in water than their non-oxyalkylated analogs. Preferably, the compounds of the invention have a solubility in water of at least 0.1%, more preferably at least 1%, and most preferably at least 10% (weight basis).

The compounds of the invention are excellent corrosion inhibitors and perform better in aqueous environments than their non-oxyalkylated analogs. Examples of environments in which the compounds of the invention are useful corrosion inhibitors include oil and gas well drilling fluids, oil and gas well bottom hole corrosion inhibitors, secondary oil recovery water flooding fluids, oilfield fracturing fluids, oilfield "produced water" disposal systems, and industrial heating and cooling water systems.

The compounds of the invention are used in corrosion inhibiting amounts. That is, an amount sufficient to reduce the level of corrosion, compared to an identical system without this corrosion inhibitor. Although the precise amount to be used will vary depending on the nature of the substrate to be protected, the nature of the corrosion problem, the nature and amount of any additional corrosion inhibitors, temperature, etc., generally the compounds of the invention will be added at 1 to 10,000 ppm (parts per million), desirably 5 to 2,000 ppm, and preferably 10 to 500 ppm, based on the weight of the aqueous system to which they are added.

The invention will be further explained in the following examples. In the examples, all parts and percentages are by weight unless otherwise stated.

EXAMPLE 1

To a pressure reactor equipped with heating and cooling means, 279.9 g (2.057 moles) of p-isopropyl phenol and 3.29 g of NAOH were added and heated to 100° to 110° C. 279.8 g (6.359 moles) of ethylene oxide was added to the reactor over a period of hours with cooling (maintaining the 100° to 110° C. temperature) to yield a product with an average of 3.1 repeating ethoxy groups per molecule. A sample was removed, additional ethylene oxide added, and the procedure repeated to yield products averaging 6.2, 9.3, 12.4, and 15.5 ethoxy units per molecule.

8.2 g (0.01 mole) of the polyoxyalkylated starting compound of the preceding paragraph having 15.5 ethoxy units was mixed with 2 g (0.06 mole) of sulfur and heated to 210° C. for about ½ hour. An unmeasured, but catalytic amount of di-o-tolyl guanidine was added and the mixture was maintained at 210° C., with stirring, for an addition 20 hours. The product was a water soluble red oil.

EXAMPLE 2

In a manner similar to Example 1, 27.2 g (0.1 mole) of the polyoxyalkylated starting compound having an average of 3.1 repeating ethoxy units was blended with 19.2 g (0.6 mole) of sulfur and heated to 210° C. for ½ hour. A catalytic amount of di-o-tolyl guanidine was added and heating continued for 24 hours. The product was water soluble.

EXAMPLE 3

In a manner similar to Example 2, 27.2 g (0.05 mole) of the polyoxyalkylated starting material an average of 9.3 repeating ethoxy units was mixed with 9.6 g (0.3 mole) of sulfur and an unmeasured amount of di-o-tolyl quanidine, and reacted as in Example 2. The product was water soluble.

EXAMPLE 4

In a manner similar to the proceeding examples, 61.2 g (0.15 mole) of the starting material having an average of 6.2 repeating ethoxy units, 27.8 g (0.87 mole) of sulfur, and an unmeasured, catalytic amount of di-o-tolyl guanidine were mixed and heated to 195° C. (±3° C.) for 24 hours. The product was water soluble.

EXAMPLE 5

The product of Example 4 was blended with an equal weight of a 50% (in water) methanol solution. The corrosion inhibiting effects of the solution were evaluated by adding 100 ppm of solution (50 ppm active ingredient) to a 0.5% NaCl solution and subjected to a $CO_2$ sparge test (ASTM G61-78) at ambient temperature. The data are shown in Table I. Upon completion of the test, the electrodes had a copper-colored coating which could easily be wiped off. A Cu ion test showed a copper deposit, indicating the presence of a good, protective film.

TABLE I

| Elapsed Time (hours:minutes) | Corrosion | |
|---|---|---|
| | Cathode (MPY[1] [mm/yy]) | Anode (MPY[1] [mm/yy]) |
| 0:00 | 120 [3.05] | 90 [2.29] |
| 0:15 | 36 [0.91] | 36 [0.91] |
| 0:30 | 30 [0.76] | 35 [0.89] |
| 1:00 | 24 [0.61] | 28 [0.71] |
| 1:40 | 22 [0.56] | 26 [0.66] |
| 2:30 | 20 [0.51] | 23 [0.58] |
| 4:00 | 17 [0.43] | 20 [0.51] |
| 5:35 | 15 [0.38] | 18 [0.46] |
| 6:15 | 15 [0.38] | 17 [0.43] |
| 6:45 | 14 [0.36] | 16 [0.41] |
| 9:45 | 8 [0.20] | 8 [0.20] |

[1]mils per year (1 mil = 0.001 inch)

What is claimed is:

1. A method of inhibiting corrosion in an aqueous system comprising adding to the aqueous system a corrosion inhibiting amount of a compound of the formula:

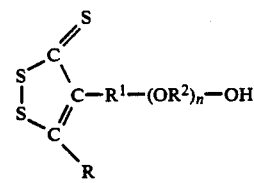

wherein R is H or a $C_1$ to $C_{12}$ alkyl moiety; $R^1$ is a $C_6$ to $C_{12}$ arylene moiety; $R^2$ is a $C_1$ to $C_4$ alkylene moiety; and n is 2 to 50.

* * * * *